US005340800A

United States Patent [19]

Liu et al.

[11] Patent Number: 5,340,800

[45] Date of Patent: Aug. 23, 1994

[54] PEPTIDE MEDICAMENTS FOR THE TREATMENT OF DISEASE

[76] Inventors: David Y. Liu, 201 Ferne Ave., Palo Alto, Calif. 94306; Zehra Kaymakcalan, 520 Norvell St., El Cerrito, Calif. 94530; Kirsten Mundy, 2450 Heatherleaf Ln., Martinez, Calif. 94553

[21] Appl. No.: 943,371

[22] Filed: Sep. 9, 1992

Related U.S. Application Data

[63] Continuation of Ser. No. 573,624, Aug. 27, 1990, abandoned.

[51] Int. Cl.[5] .......................... A61K 37/00; C07K 5/00

[52] U.S. Cl. .......................................... 514/12; 514/13; 530/324; 530/325

[58] Field of Search .................. 530/324, 325; 514/12, 514/13

[56] References Cited

U.S. PATENT DOCUMENTS 4,797,277 1/1989 Arfors ................................ 424/858

FOREIGN PATENT DOCUMENTS 0333517 9/1989 European Pat. Off. .
0346078 12/1989 European Pat. Off. .
8806592 9/1988 World Int. Prop. O. .
8809672 12/1988 World Int. Prop. O. .
9011365 10/1990 World Int. Prop. O. .
9104745 4/1991 World Int. Prop. O. .

OTHER PUBLICATIONS

Rudinger, *Peptide Hormones* (Jun. 1976) 1, 5–6.
Kishimoto et al. *Cell* vol. 48, 681 (Feb. 1987).
Kishimoto et al. Adv. In. Immun. vol. 46 (1989) ATIJO.
Abbas et al. Cell. & Mol. Immun (1991) at 158.
Hogg, N., 1989, Letters, pp. 111–114.

*Primary Examiner*—Merrell C. Cashion, Jr.
*Assistant Examiner*—B. Celsa
*Attorney, Agent, or Firm*—Albert P. Halluin; Philip J. McGarrigle, Jr.; Grant D. Green

[57] ABSTRACT

Peptide medicaments, and antibody thereto, useful for treating or preventing diseases, particularly diseases involving an inflammatory response by a host organism against infection, that are preferably derived from the $\beta$ subunit, CD18, of the leukocyte integrins, and that have the property of either interfering with, or preventing undesirable leukocyte adhesion to biological materials, particular to endothelial cells, or that interfere with, or prevent the chemotaxis of leukocytes through the endothelial cell monolayer, consequently minimizing undesirable cell/tissue leukocyte binding and thus preventing or minimizing diseases resulting therefrom.

9 Claims, 6 Drawing Sheets

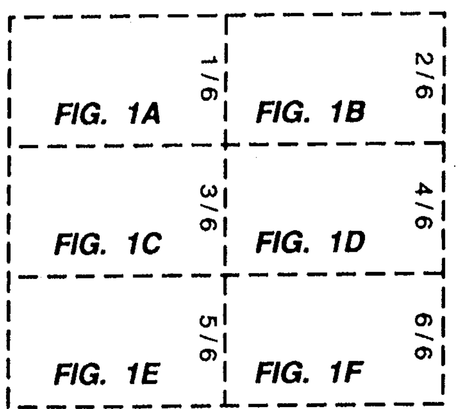

FIG._1

CAGGGCAGACTGGTAGCAAA GCCCCCACGCCCAGCCAGGA GCACCGCCGCGGACTCCAGC ACACCGAGG

124 GGG TGC GTC CTC TCT CAG GAG TGC ACG AAG TTC AAG GTC AGC AGC TGC CGG GAA
Gly Cys Val Leu Ser Gln Glu Cys Thr Lys Phe Lys Val Ser Ser Cys Arg Glu

232 CCG GGG GAT CCT GAC TCC ATT CGC TGC GAC ACC CGG CCA CAG CTG CTC ATG AGG
Pro Gly Asp Pro Asp Ser Ile Arg Cys Asp Thr Arg Pro Gln Leu Leu MET Arg

340 GAC CAC AAT GGG GGC CAG AAG CAG CTG TCC CCA CAA AAA GTG ACG CTT TAC CTG
Asp His Asn Gly Gly Gln Lys Gln Leu Ser Pro Gln Lys Val Thr Leu Tyr Leu

1

448 CCG ATC GAC CTG TAC TAT CTG ATG GAC CTC TCC TAC TCC ATG CTT GAT GAC CTC
Pro Ile Asp Leu Tyr Tyr Leu MET Asp Leu Ser Tyr Ser MET Leu Asp Asp Leu

556 GAG TCC GGC CGC ATT GGC TTC GGG TCC TTC GTG GAC AAG ACC GTG CTG CCG TTC
Glu Ser Gly Arg Ile Gly Phe Gly Ser Phe Val Asp Lys Thr Val Leu Pro Phe

```
GAC ATG CTG GGC CTG CGC CCC CCA CTG CTC GCC CTG GTG GGG CTG CTC TCC CTC
    Met Leu Gly Leu Arg Pro Pro Leu Leu Ala Leu Val Gly Leu Leu Ser Leu    17

TGC ATC GAG TCG GGG CCC GGC TGC ACC TGG TGC CAG AAG CTG AAC TTC ACA GGG
Cys Ile Glu Ser Gly Pro Gly Cys Thr Trp Cys Gln Lys Leu Asn Phe Thr Gly    53
                                                         ▲
GGC TGT GCG GCT GAC GAC ATC ATG GAC CCC ACA AGC CTC GCT GAA ACC CAG GAA
Gly Cys Ala Ala Asp Asp Ile MET Asp Pro Thr Ser Leu Ala Glu Thr Gln Glu    89
                                                                1
CGA CCA GGC CAG GCA GCA GCG TTC AAC GTG ACC TTC CGG CGG GCC AAG GGC TAC
Arg Pro Gly Gln Ala Ala Ala Phe Asn Val Thr Phe Arg Arg Ala Lys Gly Tyr   125
                          1     ▲
AGG AAT GTC AAG AAG CTA GGT GGC GAC CTG CTC CGG GCC CTC AAC GAG ATC ACC
Arg Asn Val Lys Lys Leu Gly Gly Asp Leu Leu Arg Ala Leu Asn Glu Ile Thr   161
                                      6
GTG AAC ACG CAC CCT GAT AAG CTG CGA AAC CCA TGC CCC AAC AAG GAG AAA GAG
Val Asn Thr His Pro Asp Lys Leu Arg Asn Pro Cys Pro Asn Lys Glu Lys Glu   197
```

FIG._1B

```
664   TGC CAG CCC CCG TTT GCC TTC AGG CAC GTG CTG AAG CTG ACC AAC AAC TCC AAC
      Cys Gln Pro Pro Phe Ala Phe Arg His Val Leu Lys Leu Thr Asn Asn Ser Asn
                L-56a                                           ▲
                                             5                   4
772   GAG GGT GGG CTG GAC GCC ATG ATG CAG GTC GCC GCC TGC CCG GAG GAA ATC GGC
      Glu Gly Gly Leu Asp Ala MET MET Gln Val Ala Ala Cys Pro Glu Glu Ile Gly
                                         4
880   GCG GGC GAC GGA AAG CTG GGC GCC ATC CTG ACC CCC AAC GAC GGC CGC TGT CAC
      Ala Gly Asp Gly Lys Leu Gly Ala Ile Leu Thr Pro Asn Asp Gly Arg Cys His
                                                                         2
988   CAG CTG GCG CAC AAG CTG GCT GAA AAC AAC ATC CAG CCC ATC TTC GCG GTG ACC
      Gln Leu Ala His Lys Leu Ala Glu Asn Asn Ile Gln Pro Ile Phe Ala Val Thr
                                                 P-61                    3
1096  GTG GGG GAG CTG TCT GAG GAC TCC AGC AAT GTG GTC CAT CTC ATT AAG AAT GCT
      Val Gly Glu Leu Ser Glu Asp Ser Ser Asn Val Val His Leu Ile Lys Asn Ala
          M-52
1204  CTG AAA GTC ACC TAC GAC TCC TTC TGC AGC AAT GGA GTG ACG CAC AGG AAC CAG
      Lau Lys Val Thr Tyr Asp Ser Phe Cys Ser Asn Gly Val Thr His Arg Asn Gln

1312  AAG GTC ACG GCC ACA GAG TGC ATC CAG GAG CAG TCG TTT GTC ATC CGG GCG CTG
      Lys Val Thr Ala Thr Glu Cys Ile Gln Glu Gln Ser Phe Val Ile Arg Ala Leu

1420  CGG GAC CAG AGC AGA GAC CGC AGC CTC TGC CAT GGC AAG GGC TTC TTG GAG TGC
      Arg Asp Gln Ser Arg Asp Arg Ser Leu Cys His Gly Lys Gly Phe Leu Glu Cys

1528  CAG GGC CGG AGC AGC CAG GAG CTG GAA GGA AGC TGC CGG AAG GAC AAC AAC TCC
      Gln Gly Arg Ser Ser Gln Glu Leu Glu Gly Ser Cys Arg Lys Asp Asn Asn Ser
                              P-18                            ▲
```

FIG._1C

```
CAG TTT CAG ACC GAG GTC GGG AAG CAG CTG ATT TCC GGA AAC CTG GAT GCA CCC
Gln Phe Gln Thr Glu Val Gly Lys Gln Leu Ile Ser Gly Asn Leu Asp Ala Pro     233
              4         5

TGG CGC AAC CTC ACG CGG CTG CTG GTG TTT GCC ACT GAT GAC GGC TTC CAT TTC
Trp Arg Asn Val Thr Arg Leu Leu Val Phe Ala Thr Asp Asp Gly Phe His Phe     269
         ▲                                              M-58

CTG GAG GAC AAC TTG TAC AAG AGG AGC AAC GAA TTC GAC TAC CCA TCG GTG GGC
Leu Glu Asp Asn Leu Tyr Lys Arg Ser Asn Glu Phe Asp Tyr Pro Ser Val Gly     305
                                              2

AGT AGG ATG GTG AAG ACC TAC GAG AAA CTC ACC GAG ATC ATC CCC AAG TCA GCC
Ser Arg Met Val Lys Thr Tyr Glu Lys Leu Thr Glu Ile Ile Pro Lys Ser Ala     341
                      3                            3

TAC AAT AAA CTC TCC TCC AGG GTC TTC CTG GAT CAC AAC GCC CTC CCC GAC ACC
Tyr Asn Lys Leu Ser Ser Arg Val Phe Leu Asp His Asn Ala Leu Pro Asp Thr     377
                                            L-65

CCC AGA GGT GAC TGT GAT GGG GTG CAG ATC AAT GTC CCG ATC ACC TTC CAG GTG
Pro Arg Gly Asp (Cys) Asp Gly Val Gln Ile Asn Val Pro Ile Thr Phe Gln Val     413

GGC TTC ACG GAC ATA GTG ACC GTG CAG GTT CTT CCC CAG TGT GAG TGC CGG TGC
Gly Phe Thr Asp Ile Val Thr Val Gln Val Leu Pro Gln (Cys) Glu (Cys) Arg (Cys)     449

GGC ATC TGC AGG TGT GAC ACT GGC TAC ATT GGG AAA AAC TGT GAG TGC CAG ACA
Gly Ile (Cys) Arg (Cys) Asp Thr Gly Tyr Ile Gly Lys Asn (Cys) Glu (Cys) Gln Thr     485
                           P-20

ATC ATC TGC TCA GGG CTG GGG GAC TGT GTC TGC GGG CAG TGC CTG TGC CAC ACC
Ile Ile (Cys) Ser Gly Lau Gly Asp (Cys) Val (Cys) Gly Gln (Cys) Leu (Cys) His Thr     521
```

FIG._1D

```
1636  AGC GAC GTC CCC GGC AAG CTG ATA TAC GGG CAG TAC TGC GAG TGT GAC ACC ATC
      Ser Asp Val Pro Gly Lys Leu Ile Tyr Gly Gln Tyr Cys Glu Cys Asp Thr Ile
                                              L-56b

1744  TTC TGC GGG AAG TGC CGC TGC CAC CCG GGC TTT GAG GGC TCA GCG TGC CAG TGC
      Phe Cys Gly Lys Cys Arg Cys His Pro Gly Phe Glu Gly Ser Ala Cys Gln Cys

1852  GGC CGG TGT CGC TGC AAC GTA TGC GAG TGC CAT TCA GGC TAC CAG CTG CCT CTG
      Gly Arg Cys Arg Cys Asn Val Cys Glu Cys His Ser Gly Tyr Gln Leu Pro Leu

1960  GAG TGC CTG AAG TTC GAA AAG GGC CCC TTT GGG AAG AAC TGC AGC GCG GCG TGT
      Glu Cys Leu Lys Phe Glu Lys Gly Pro Phe Gly Lys Asn Cys Ser Ala Ala Cys
                                                      ▲

2068  GAC TCA GAG GGC TGC TGG GTG GCC TAC ACG CTG GAG CAG CAG GAC GGG ATG GAC
      Asp Ser Glu Gly Cys Trp Val Ala Tyr Thr Leu Glu Gln Gln Asp Gly MET Asp

2176  GCC GCC ATC GTC GGG GGC ACC GTG GCA GGC ATC GTG CTG ATC GGC ATT CTC CTG
      Ala Ala Ile Val Gly Gly Thr Val Ala Gly Ile Val Leu Ile Gly Ile Leu Leu

2284  TTT GAG AAG GAG AAG CTC AAG TCC CAG TGG AAC AAT GAT AAT CCC CTT TTC AAG
      Phe Glu Lys Glu Lys Leu Lys Ser Gln Trp Asn Asn Asp Asn Pro Leu Phe Lys

2403  GAAGACAAGGCCGTCAGGACCCACCATGTCTGCCCCATCACGCGGCCGAGACATGGCTTGGCCACAGCTCTT

2546  CTTCTGGGGGCTCGTCGGGGGACAGCTCCACTCTGACTGGCACAGTCTTTGCATGGAGACTTGAGGAGGGC

2689  ATTTATTTACATTTAAACTTGTCAGGGTATAAAATGACATCCCATTAATTATATTGTTAATCAATCACGTGT
```

FIG._1E

```
AAC TGT GAG CGC TAC AAC GGC CAG GTC TGC GGC GGC CCG GGG AGG GGG CTC TGC
Asn Cys Glu Arg Tyr Asn Gly Gln Val Cys Gly Gly Pro Gly Arg Gly Leu Cys    557

GAG AGG ACC ACT GAG GGC TGC CTG AAC CCG CGG CGT GTT GAG TGT AGT GGT CGT
Glu Arg Thr Thr Glu Gly Cys Leu Asn Pro Arg Arg Val Glu Cys Ser Gly Arg    593

TGC CAG GAG TGC CCC GGC TGC CCC TCA CCC TGT GGC AAG TAC ATC TCC TGC GCC
Cys Gln Glu Cys Pro Gly Cys Pro Ser Pro Cys Gly Lys Tyr Ile Ser Cys Ala    629

CCG GGC CTG CAG CTG TCG AAC AAC CCC GTG AAG GGC AGG ACC TGC AAG GAG AGG
Pro Gly Leu Gln Leu Ser Asn Asn Pro Val Lys Gly Arg Thr Cys Lys Glu Arg    665

CGC TAC CTC ATC TAT GTG GAT GAG AGC CGA GAG TGT GTG GCA GGC CCC AAC ATC
Arg Tyr Leu Ile Tyr Val Asp Glu Ser Arg Glu Cys Val Ala Gly Pro Asn Ile    701

CTG GTC ATC TGG AAG GCT CTG ATC CAC CTG AGC GAC CTC CGG GAG TAC AGG CGC
Leu Val Ile Trp Lys Ala Leu Ile His Leu Ser Asp Leu Arg Glu Tyr Arg Arg    737

AGC GCC ACC ACG ACG GTC ATG AAC CCC AAG TTT GCT GAG AGT TAG GAGCACTTGGT
Ser Ala Thr Thr Thr Val MET Asn Pro Lys Phe Ala Glu Ser  •                 769

GAGGATGTCACCAATTAACCAGAAATCCAGTTATTTTCCGCCCTCAAAATGACAGCCATGGCCGGCCGGTG

TTGAGGTTGGTGAGGTTAGGTGCGTGTTTCCTGTGCAAGTCAGGACATCAGTCTGATTAAAGGTGGTGCCA

ATAGAAAAAAAAATAAAACTTCAAT                                                  2776
```

FIG._1F

PEPTIDE MEDICAMENTS FOR THE TREATMENT OF DISEASE

This is a continuation of co-pending application Ser. No. 07/573,624 filed on Aug. 27, 1990, now abandoned.

FIELD OF THE INVENTION

This invention is in the area of molecular biology/biochemistry and presents peptides having defined amino acid sequences that are useful medicaments, particularly when employed as anti-inflammatory prophylactics or therapeutics.

BACKGROUND OF THE INVENTION

During an inflammatory response peripheral blood leukocytes, consisting of neutrophils and monocytes, bind to and migrate thru the vascular endothelial cell layer and cross the basement membrane in response to chemotactic factors, and enter the infected tissue where they are effective at controlling or ridding the organism of the infection. When a host defense system responds properly to an infection, the inflammatory response is tightly controlled such that leukocytes enter only the infected area, and consequently do not damage healthy tissue. In certain disease conditions, particularly sepsis, leukocyte action is not tightly controlled, and consequently can cause extensive vascular damage arising as a result of the release of oxygen-derived free radicals, as well as proteases and phospholipases from the neutrophils which thus can cause significant cellular and tissue injury. Harlan, J. M., 1987, *Acta Med Scand Suppl.*, 715:123; Weiss, S., 1989, *New England J. of Med.*, 320:365. For example, sepsis associated neutrophil-mediated endothelial injury has been linked to loss of vascular integrity, thrombosis, and tissue necrosis.

The initial event that leads to neutrophil damage of endothelial cells is the adhesion of neutrophils to the endothelial cell surface. In significant part this is medicated by cellular adhesion molecules associated with the neutrophils that cause them to bind to the endothelial cell surface. The neutrophil adhesion molecules bind to a molecule on the surface of endothelial cells termed ICAM-1 (Intercellular Adhesion Molecule 1). To date, a partial list of the adhesion molecules that have been identified that are involved in this reaction are lymphocyte function-associated antigen-1 (LFA-1), macrophage antigen-1 (MAC-1), also termed MO-1, OKM-1 and complement receptor type-3 (CR-3), and p150,95, also termed complement receptor type-4 (CR-4) and Leu M-5. These molecules collectively have been termed the LFA-1 family, leukocyte adhesion proteins, leuCAM, and the leukocytes integrins. All three molecules are $\alpha$-$\beta$ heterodimers. The $\beta$ subunit is identical in the three molecules, while the $\alpha$ subunit differs. Kurzinger, K., and Springer, T. A., 1982, *J. of Biol. Chem.*, 257:12412; Sanchez-Madrid, F., et al., 1983, *J. Exp. Med.*, 158:1785; Trowbridge, I. S., and Omary, M. B., 1981, *PNAS* (*USA*), 78:3039.

The three leukocyte integrins are predominately expressed by immune cells. For instance, LFA-1 is found on virtually all immune cells. Kurzinger, K. and Springer, T. A., supra. MAC-1 is expressed by monocytes, macrophages, granulocytes, large granular lymphocytes, and immature and CD-5+B cells. De La Hera, A., et al. 1988, *Eur. J. of Immun.*, 18:1131. p150,95 protein shares the same cell type distribution as MAC-1, but is further expressed by activated lymphocytes, as well as hairy cell leukemia. It is a marker of the latter disease. Schwarting, R., et al., 1985, *Blood*, 65:974; Miller, B. A., et al., 1985, *J. of Immun.*, 134:3286.

Studies have implicated the leukocyte integrins in cellular adhesion events. For example, LFA-1 is involved in antigen-dependent and antigen-independent interactions of immune cells. Springer, T. A., et al., 1987, Annual Review Immun., 5:223; Martz, E., 1986, *Hum. Immunology*, 18:3. Most telling are studies utilizing a monoclonal antibody to LFA-1, which have revealed that binding to LFA-1 by monoclonal antibody partially or totally inhibits T lymphocytes adherence to endothelial cells (Mentzer, S. J., et al. 1986, J. of Cell Physiol., 126:285), fibroblasts (Dustin, N. L., et al., 1986, *J. of Immun.*, 137:245), epidermal keratinocytes (Dustin, N. L., et al., 1988, *J. of SubBiology*, 107:321), and hepatocytes (Roos, E., and Roossien, F., 1987, *J. of SubBiology*, 105:553).

The role of MAC-1 in cellular adhesion was initially demonstrated also using monoclonal antibodies. Such studies show that MAC-1 binds to C3bi-coated erythrocytes, and that such binding could be inhibited by monoclonal antibodies to MAC-1. Beller, B. I., et al., 1982, *J. of Exp. Med.*, 156:1000. Additionally, MAC-1 has been shown to be involved in macrophage binding to *Leishmania Promastigotes*, *E. coli*, and *Histoplasma Capsulatum*. Mosser, D. and Edelson, P., 1985, *J. of Immun.*, 135:2785; Wright, S. and Jong, M., 1986, *J. of Exp Med.*, 164:1876; Bullock, W. and Wright, S., 1987, *J. of Exp. Med.*, 165:195. Other studies have shown that MAC-1 is involved in neutrophil and monocyte chemotaxis, as well as adherence to glass and plastic surfaces, and to endothelial and epithelial cell monolayers.

p150,95 is reported to be significantly involved in peripheral blood monocyte adhesion to substrates and endothelial cells, phagocytosis of latex particles, and chemotaxis. Keizer, et al., 1987, *Eur. J. of Immun.*, 17:1317; te Velde, A., et al., 1987, *Immunology*, 61:261. Further, studies using a monoclonal antibody that is directed to p150,95 have shown it to be utilized in conjugate formation by cytotoxic T lymphocytes.

The studies described above, as well as additional studies suggest that the leukocyte integrins function as general adhesion proteins to effect immune cell function. Further, the studies described above have used monoclonal antibodies directed either to the $\alpha$ or $\beta$ subunits of the three integrins. For the most part, these studies have shown the common $\beta$ subunit to play the predominant role in the adhesion-related functions of these molecules. Recently the cDNA clone that encodes the $\beta$ subunit of human LFA-1, MAC-1, and p150,95 has been isolated. Kishimoto, T., et al., 1987, *Cell*, 48:681; and Law, S. K. A. et al., 1987, *EMBO J.*, 6:915–919.

As mentioned above, inflammation is a significant part of an organism's defense to infection and may be a cause of injury of extravascular tissue. Moreover, in certain instances there is an uncontrolled inflammatory response, such as that observed in septic shock, which may contribute to the pathogenesis of the disease. Leukocytes have been implicated as being, at least in part, responsible for the damage associated with acute ischemic shock by releasing reactive oxygen metabolites, proteases, and phospholipases at the disease sites. This is supported by studies which have shown that animals depleted of peripheral blood leukocytes show significantly reduced damage from myocardial ischemia and reperfusion. Further, reperfusion injury can be minimized by in vivo administration of MAC-1 monoclonal antibodies. Finally, a rabbit model of hemorrhagic shock and resuscitation reveals that monoclonal antibodies against the β subunit of MAC-1 exhibited a protective effect to liver and the asternal intestinal track. Simpson, et al., *J. of Clinical Invest.*, 1988, 81:624; Vedder, N. and Harlan, J., 1988, *J. of Clinical Invest.*, 81:676. Taken together, these results suggest significant therapeutic value for reagents that block the adhesion of leukocytes via the three leukocyte integrins in controlling tissue and organ injury resulting from a number of disease situations including myocardial infarction, hemorrhagic shock, and other events that cause ischemia that are followed by reestablishing normal circulatory blood flow.

Finally, it is noteworthy that ICAM-1, the endothelial cell receptor for integrin binding, is also the receptor for rhinovirus binding. Staunton, D., et al., 1990, *Cell,* 61:243. Rhinovirus is a member of the picornavirus family and is responsible for about 50% of common colds. Sperber, S. and Hayden, F. (1988) Antimicrob. Agents Chemother. 32, vol. 409, page 32. A prophylactic approach to preventing the common cold is to interfere with the binding of rhinovirus to cell bound ICAM-1. Indeed, a soluble form of ICAM-1 has recently been reported to be effective. Marlin, S. D., et al., 1990, *Nature,* 344:70.

SUMMARY OF THE INVENTION

In one aspect, the invention presented herein describes peptides that prevent or interfere with undesirable binding of cells or virions to cells or tissues that express an appropriate membrane receptor (e.g., ICAM) for the cells or virions and thus prevents or minimizes disease resulting from the binding of the cells or virions.

A second aspect of the invention describes peptides that have sequence homology to particular regions of the β subunit, CD18, of the leukocyte integrins that compete with the integrins to prevent undesirable tissue binding of leukocytes or virions thereto, as well as interfere with leukocyte chemo-attractiveness to the tissue, thereby preventing or minimizing disease to the tissue resulting from leukocyte or virion binding.

A third aspect of the invention is the description of peptides that inhibit or prevent leukocyte adhesion, without affecting leukocyte chemotaxis, thus preventing undesirable tissue binding of the leukocytes thereto, and consequently preventing or minimizing disease to the tissue resulting from leukocyte binding.

A fourth aspect of the invention is the description of methods for prophylactically or therapeutically treating patients suffering from various diseases with peptides that interfere with leukocyte or virion cell adhesion and/or leukocyte chemotaxis.

A fifth aspect of the invention is the description of methods for prophylactically or therapeutically treating patients suffering from various diseases with peptides that interfere with leukocyte cell adhesion and/or chemotaxis, particularly diseases caused by rhinovirus infection.

A sixth aspect of the invention is the description of antibody to CD18 peptides, and prophylactic and therapeutic applications of the antibody.

Yet another aspect of the invention is the description of peptides that inhibit the cellular adhesion properties of leukocytes, wherein said peptides are not readily hydrolyzable, and thus exhibit a prolonged in vivo circulation time.

These and other aspects of the invention will be apparent upon a full consideration of the invention as presented below.

BRIEF DESCRIPTION OF THE DRAWINGS

FIG. 1 is a diagram which depicts the assembly of FIG. 1A through FIG. 1F. FIGS. 1A through 1F set forth the DNA and amino acid sequences of the β subunit, CD18, of the leukocyte integrins.

Underlined regions correspond to peptides that were synthesized and tested for activity in the leukocyte/endothelial cell adhesion assay. Smaller peptides within a region were also synthesized and tested for activity. Each peptide is denoted by the number in the figure, that is 1 through 6, and a second number that refers to the number of amino acids in the peptide. Thus, 1–26 refers to a peptide from region 1 with 26 amino acids. Since region 1 consists of only 26 amino acids, 1–26 denotes a peptide that spans the entire region. 1–15, however, refers to a peptide from region 1 consisting of 15 amino acids. The peptides are numbered from the carboxyl to the amino terminal end of the molecule.

FIGS. 1A, 1B, 1C, 1D, 1E, and 1F are assembled to make FIG. 1, as shown in the diagram in FIG. 1A. FIG. 1A contains the upper left one-sixth of the sequence depicted.

FIG. 1B contains the upper right one-sixth of the sequence depicted.

FIG. 1C contains the middle left one-sixth of the sequence depicted.

FIG. 1D contains the middle right one-sixth of the sequence depicted.

FIG. 1E contains the bottom left one-sixth of the sequence depicted.

FIG. 1F contains the bottom right one-sixth of the sequence depicted.

TABLES

Table 1 shows the amino acid sequence of various CD18 peptides that were tested for their capacity to inhibit polymorphonuclear leukocyte adhesion to endothelial cells.

Table 2 shows the inhibitory effect of several CD18 peptides on polymorphonuclear leukocyte adhesion over a concentration range of $10^{-4}$ to $10^{-8}$ M. It is apparent that 4–29 is most effective at $10^{-5}$ molar.

Table 3 shows the effects of the peptide 4–29 on polymorphonuclear leukocyte adhesion over a concentration range of $10^{-4}$ to $10^{-8}$ M using polymorphonuclear leukocytes from different human donors, and after the peptide had been stored under various conditions.

Table 4 shows the effects of the peptide 4–15 on polymorphonuclear leukocyte adhesion over a concentration range of $10^{-4}$ to $10^{-6}$ M, and using polymorphonuclear leukocytes from different donors.

Table 5 shows the chemotaxis inhibitory activity of the CD18 peptides, 1–26, 2–24, 3–29, 4–29, 5–24, and 6–25.

Table 6 shows the chemotaxis inhibitory activity of the CD18 peptide, 4–29.

DETAILED DESCRIPTION OF THE INVENTION

The invention described herein draws on previously published work. By way of example, such work consists of scientific papers, patents or pending patent applications. All of these publications and applications, cited previously or below, are hereby incorporated by reference.

The instant invention is composed of several unique methods and compositions. Each aspect of the invention will now be discussed separately.

A. CD18 Peptides

Peptides have been discovered that prevent or interfere with cell-cell or cellvirion adhesion events that are useful medicaments for treating a variety of diseases, preferably diseases resulting from untoward adhesion of leukocytes or rhinovirus. These peptides have amino acid sequence homology to regions of the beta subunit of the leukocyte intergrins, CD18.

Preferred is a peptide that incorporates the following 5 amino acids:

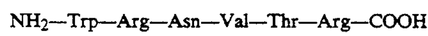

NH2—Trp—Arg—Asn—Val—Thr—Arg—COOH

More preferred is the above peptide incorporated into a larger peptide that has the following sequence:

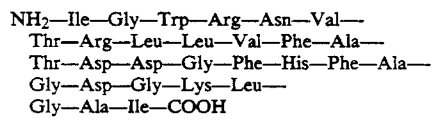

NH2—Ile—Gly—Trp—Arg—Asn—Val—
Thr—Arg—Leu—Leu—Val—Phe—Ala—
Thr—Asp—Asp—Gly—Phe—His—Phe—Ala—
Gly—Asp—Gly—Lys—Leu—
Gly—Ala—Ile—COOH

Most preferred is the above peptide incorporated into a larger peptide that has the following sequence:

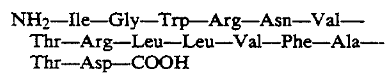

NH2—Ile—Gly—Trp—Arg—Asn—Val—
Thr—Arg—Leu—Leu—Val—Phe—Ala—
Thr—Asp—COOH

FIG. 1 shows the amino acid sequence of the beta subunit of the leukocyte integrins, CD18, and those peptides that interfere with leukocyte or virion adhesion are underlined. Specifically, the peptides were tested for their ability to compete with and prevent adhesion of leukocytes to activated endothelial cells. Additionally, the ability of these peptides to inhibit leukocyte chemotaxis was determined.

The peptides described above can be made by techniques well known in the art, such as, for example, the Merrifield solid-phase method described in *Science*, 232:341–347 (1985). The procedure may use commercially available synthesizers such as a Biosearch 9500 automated peptide machine, with cleavage of the blocked amino acids being achieved with hydrogen fluoride, and the peptides purified by preparative HPLC using a Waters Delta Prep 3000 instrument, on a 15–20 μm Vydac C4 PrepPAK column.

It will be appreciated by those skilled in the art that although the precise chemical structure of the preferred CD18 peptides are shown herein, that particular alterations to the structure may be desired depending on a number of factors, a key factor being the use to which the peptide is being put to. For example, for convenience of administration to a patient a peptide may be formulated as an acidic or basic salt, or in neutral form. Further, the primary amino acid sequence of the protein may be augmented by derivatization using sugar moieties (glycosylation) or by other supplementary molecules such as lipids, phosphate, acetyl groups and the like, as well as by conjugation with saccharides, polyethylene glycols (PEGs) and polyoxyethylene glycols (POGs). Such modifications are included in the definition of peptide herein so long as the activity of the peptide, as defined above, is not destroyed. It is expected, of course, that such modifications may quantitatively or qualitatively affect the activity, either by enhancing or diminishing the activity of the protein in the various assays.

Furthermore, it will be particularly appreciated by those skilled in this art, that peptide medicaments that have an increased in vivo residence time may be advantageous for particular applications. The in vivo residence time of peptides may be increased using methods known in the art, and two exemplary methods include synthesizing peptides that have substantially non-hydrolyzable peptide bonds, or that are bound to, or associated with bio-compatible polymers. Exemplary polymers are described by Ulbrich, K., et al., 1986, *Makromol. Chem.*, 187:1131; and Rihova, B., 1986, *J. of Chromatography*, 376:221.

It will be appreciated by those skilled in the art that the peptides described herein can be administered to mammals, including humans, either alone or in combination with other anti-inflammatory agents, or they may be combined with various pharmaceutically acceptable diluents or carriers. Such are widely known to those skilled in the art and are formulated according to standard pharmaceutical practices.

Exemplary diluents include physiologic saline, or buffered saline, as well as Ringer's and dextrose injection fluid, and dextrose saline and lactated Ringer's injection or diluent solutions containing additional therapeutic agents, preferably antibiotics or antibodies known to be efficacious in the treatment of inflammatory conditions.

B. Leukocyte Preparation/Labelling

Leukocyte adherence can be measured using several assays known in the art, and the preferred assay is described by Charo, et al., 1985, *Blood*, 65:473. Briefly, the assay consists of labelling leukocytes with an appropriate label, incubating them with endothelial cells and determining the number of leukocytes that adhere. Preferably the cells are labelled with a gamma ray emitting isotope and the preferred labels are $^{111}$Indium-oxide or $^{51}$chromium.

Leukocytes may be isolated from human donors using standard techniques. This generally consists of isolating blood in a physiologically balanced salt solution containing an appropriate anticoagulant, and separating the leukocytes by an appropriate separation step, preferably on Ficoll-Hypaque gradients. Contaminating erythrocytes can be removed by hypotonic lysis. The resulting leukocytes are suspended in a physiologically buffered solution, pH 7.4. The preferred physiological buffered solution is Hank's balanced salt solution that is calcium and magnesium free.

The isolated leukocytes can then be labelled by incubating them for an appropriate time, generally 15 minutes, with the desired radioisotope at a predetermined concentration. The radiolabelled cells are washed to remove unincorporated label, and then suspended in an appropriate solution to perform the adhesion assay described below.

C. Endothelial Cell Preparation/Culture

Endothelial cells can be prepared from a number of sources and by several techniques known in the art. Preferably they are obtained from human umbilical veins using the procedure of Charo et al., above. Generally, endothelial cells are isolated by enzymatic digestion of the umbilical veins using, preferably, collagenase as described by Jaffe, E. A., et al., 1973, *J. of Clin. Invest*, 52:2745. The cells are grown on an appropriate tissue culture substratum, preferably gelatine-coated surfaces.

The endothelial cells may be grown in a variety of tissue culture media containing appropriate supplements such as an appropriate concentration of fetal calf serum, and other supplements/additives routinely utilized by those skilled in this art that are recognized as being favorable for endothelial cells. The endothelial cells may be passaged with a dilute solution of an appropriate protease, and if desired a metal ion chelator. Preferably a solution consisting of 0.05 to 0.25% trypsin and 0.02% EDTA is used. To ensure that the cells are indeed endothelial cells, they are tested by immunofluorescence for Factor VIII antigen, a known endothelial cell marker.

D. Leukocyte/Endothelial Cell Adhesion Assay

Leukocyte adherence to endothelial cell monolayers may be determined as follows. Early passage endothelial cells, generally not beyond the fifth passage, are cultured on an appropriate substratum and in a suitable cell culture medium. The culture substratum is preferably pre-coated with an appropriate substance that enhances the adherence of the endothelial cells. Several such substances are known including fibronectin, poly-L-lysine, gelatin and laminin. Fibronectin is preferred. An appropriate culture substratum is a 96 well micro titer plate, and a suitable medium is Medium 199 containing fetal calf serum and other supplements known to be beneficial for the growth and maintenance of endothelial cells that are well known to those skilled in the art. Prior to adding a predetermined number of labelled leukocytes, the endothelial cell monolayer is washed with a physiologically balanced salt solution containing a reduced amount of fetal calf serum, preferably 1%. The preferred solution is RPMI supplemented with 1% fetal calf serum.

The endothelial cell monolayer containing added leukocytes is incubated for a time sufficient to permit maximum adherence of the leukocytes, and preferably this is conducted at 37° C. for 30 minutes in an appropriate cell culture atmosphere. Generally this would consist of growing and incubating the cells for the assay period in 5% $CO_2$, 95% air, and 95% humidity. Next, non-adherent leukocytes are removed by any number of techniques known in the art, and the number of leukocytes adherent to the endothelial cell monolayers determined by measuring the amount of radioisotope associated with the endothelial cell monolayer. Controls are run that take into account basal binding, i.e., binding to endothelial cells not activated with TNF.

In a typical experiment run in quadruplicate, the assay is highly reliable, giving standard deviations less than 10%, and usually less than 5%, of mean values. Typically the results are expressed as the percent of leukocytes added to the endothelial cells that remain adherent after non-adherent cells have been removed.

Using the above assay, typically peptides to be tested are added over a range of concentrations, preferably from $10^{-4}$M to $10^{-7}$M. The peptides are synthesized as described above, lyophilized and dissolved in 15–25 $\mu$l of dimethylsulfoxide. This volume is then suitably diluted in an appropriate medium, preferably RPMI containing 1% fetal calf serum to give the desired final concentration to be tested.

The endothelial cells were activated with 125 U/ml of TNF having a specific activity of $2\times10^7$ U/mg for at least 4 hours in RPMI with 1% fetal calf serum prior to the addition of the leukocytes. TNF causes the induction of ICAM expression on endothelial surfaces which is a receptor for leukocyte integrin binding.

E. Chemotaxis

The materials and methods for ascertaining the chemotactic inhibitory properties of peptides are generally known in the art, and the preferred procedure is described by Capsoni, et al., 1989, *J. of Immunol. Meth.*, 120:125. Generally, chemotaxis is determined by positioning the leukocytes and a chemotactic substance on opposite sides of a membrane in appropriate culture media. The preferred apparatus for doing a chemotaxis assay is produced by Costar Corporation, Cambridge, Mass., and is termed the trans-well cell culture apparatus. The size of the membrane is selected so that the leukocytes do not have unrestricted access to the substance; rather if a chemotactic response is elicited the leukocytes adhere to, and migrate into and through the filter. If a substance is being tested for inhibitory activity this can be achieved by combining it with the leukocytes or the chemotactic substance.

The procedure of Capsoni, et al., above, was followed with the following modifications. Leukocytes may be isolated and labelled with $^{111}$Indium as described for the adhesion assay, above. The cells are resuspended after labelling in an appropriate cell culture medium at about $5\times10^6$ cells/ml. Next, a desired amount of the cell suspension is mixed with a predetermined amount of the peptide(s) to be tested for inhibitory activity, and the mixture added to an appropriate filter device. Three $\mu$m-pore membranes are situated in the wells of a 24 trans-well tissue culture plate. The cell/inhibitory peptide mixture is incubated for a short time at 37° C. to acclimate the cells to the membrane surface, and to provide sufficient time for them to settle onto the membrane surface. Next, inserts are set in wells containing cell culture media. The media contains zymosan-activated human serum at about 0.5%. Zymosan activation generates complement-derived chemotactic factors which attract the leukocytes through the pores of the membrane. This media was also prewarmed for an appropriate time prior to addition to the cell culture wells. After a 30 minute incubation period at 37° C., the number of leukocytes that have migrated through the membrane filter, in the presence or absence of CD18 peptides, is readily determined by counting the amount of $^{111}$Indium present in the media. This may be facilitated by adding an appropriate detergent at an appropriate concentration to the media in the wells prior to removing an aliquot for counting. In this way, the inhibitory activities of the peptide being tested could be determined.

F. Inhibition of Rhinovirus Binding By CD18 Peptides

The effect of CD18 peptides on rhinovirus binding can be determined using known methods and materials as described by Abraham, G. and Colonno, R. J. (1984) J. Virol. vol. 51 page 340, with modifications as described by Marlin, S. D. et al., (1990) Nature, vol. 344. page 70. Briefly, the procedure consists of radiolabelling rhinovirus by growing virally infected cells in culture media containing a suitable radioisotope, and isolating the virus from the culture media using methods known in the art. Particularly effective is precipitation of virions from the culture media using polyethylene glycol, followed by pelleting the virions through a 30% sucrose step gradient.

The radiolabelled virions can be employed in a cell adhesion assay, using cells that express ICAM-1. The preferred cells are either endothelial cells prepared as described above or HeLa cells as described by Abraham, G. and Colonno, R. J., above. The assay can be conducted essentially as described for measuring neutrophil adhesion to endothelial cells, with the addition of the appropriate CD18 peptide to the assay mixture. It would be ascertained that those peptides that bind to ICAM-1 and prevent virion binding are readily identified by counting the number of virions that bind to the cell monolayer in the presence of the peptides.

G. Antibody to CD18 Peptides

Antibody, either polyclonal or monoclonal or recombinant, the latter preferably humanized, can be generated against the inhibitory peptides. Such antibody would be used for binding to the CD18 molecule present on leukocytes, and thus interfere with, or prevent the adhesion of leukocytes to endothelium.

Monoclonal antibody may be produced using the general procedures described by Kohler, G. and Milstein, C., 1975, *Nature*, 256:495, which have been modified over the years as is known in the art. These initial studies involved fusing murine lymphocytes and drug selectable plasmacytomas to produce hybridomas. Subsequently, the technique has been applied to produce hybrid cell lines that secrete human monoclonal antibodies. The latter procedures are generally described by Abrams, P., 1986, *Methods in Enzymology*, 121:107, but other modifications are known to those skilled in the art.

Regardless of whether murine or human antibody is produced, the antibody secreting cells are combined with the fusion partner and the cells fused via electrofusion or with a suitable fusing agent, preferably polyethylene glycol, and more preferably polyethylene glycol 1000. The latter is added to a cell pellet containing the antibody secreting cells and the fusion partner in small amounts over a short period of time accompanied with gentle agitation. After the addition of the fusing agent, the cell mixture is washed to remove the fusing agent and any cellular debris, and the cell mixture consisting of fused and unfused cells seeded into appropriate cell culture chambers containing selective growth media. After a period of one to three weeks, hybrid cells are apparent, and may be identified as to antibody production and subcloned to ensure the availability of a stable monoclonal cell line.

The preferred antibody is human monoclonal antibody which can be prepared from lymphocytes sensitized with a peptide either in vivo or in vitro by immortalization of antibody-producing hybrid cell lines, thereby making available a permanent source of the desired antibody. In vivo immunization techniques are well known in the art, while in vitro techniques are generally described by Luben, R. and Mohler, M., 1980, *Molecular Immunology*, 17:635, Reading, C. *Methods in Enzymology*, 121 (Part One):18, or Voss, B., 1986, *Methods in Enzymology*, 121:27. A number of in vitro immunization systems have been shown to be effective for sensitizing human B-cells. Reading, C., 1982, *J. of Immun. Methods*, 53:261.

Sensitized lymphocytes can be immortalized by viral transformation. The preferred viral transformation technique for human lymphocytes involves the use of Epstein-barr virus. The virus is capable of transforming human B-cells, and has been used to generate human monoclonal antibodies. Crawford, D. et al., 1983, *J. of General Virology*, 64:697; Kozbor, V. and Roder, J., 1983, *J. Immun. Today*, 4:72.

Another procedure whereby sensitized lymphocytes may be immortalized consist of a combination of the above two techniques, that is viral transformation and cell fusion. The preferred combination consist of transforming antibody secreting cells with Epstein-barr virus, and subsequently fusing the transformed cells to a suitable fusion partner. The fusion partner may be a mouse myeloma cell line, a heteromyeloma line, or a human myeloma line, or other immortalized cell line. PCT Patent Application No. 81/00957; Schlom et al., 1980, *PNAS USA*, 77:6841; Croce et al., 1980, *Nature*, 288:488. The preferred fusion partner is a mouse-human hetero-hybrid, and more preferred is the cell line designated F3B6. This cell line is on deposit with the American Type Culture Collection, Accession No. HB8785. It was deposited Apr. 18, 1985. The procedures for generating F3B6 are described in European Patent Application, Publication No. 174,204. Techniques applicable to the use of Epstein-Barr virus transformation and the production of immortal antibody secreting cell lines are presented by Roder, J. et al., 1986, *Methods in Enzymology*, 121:140. Basically, the procedure consist of isolating Epstein-Barr virus from a suitable source, generally an infected cell line, and exposing the target antibody secreting cells to supernatants containing the virus. The cells are washed, and cultured in an appropriate cell culture medium. Subsequently, virally transformed cells present in the cell culture can be identified by the presence of the Epstein-Barr viral nuclear antigen, and transformed antibody secreting cells can be identified using standard methods known in the art.

Antibodies to peptides are produced using standard coupling procedures to suitable carrier molecules as is known in the art. The preferred procedures and compositions are described in U.S. Pat. No. 4,762,706, issued Aug. 9, 1988, to McCormick, et al. For example, antibodies are produced by injecting a host animal such as rabbit, rat, goat, mouse, etc., with the peptide or peptide fragment. Before injection, the peptides are first conjugated with a suitable carrier molecule, preferably keyhole limpet hemocyanin (KLH) or bovine serum albumin (BSA). The conjugation is preferably achieved via a sulfhydryl group in a cysteine residue on the peptide. If a peptide lacks a cysteine residue it may be added using known methods.

A heterobifunctional crosslinking reagent may be used to couple the carrier protein and the desired peptide. The preferred coupling reagent is N-maleimido-6-amino caproyl ester of 1-hydroxy-2-nitro-benzene-4-sulfonic acid sodium salt, and its preparation and used are known in the art, and is described in U.S. Pat. No. 4,762,706.

Having described what the applicants believe their invention to be, the following examples are presented to illustrate the invention, and are not to be construed as limiting the scope of the invention. For example, variation in the source, type, or method of producing antibodies; different labels and/or signals; test supports of different materials and configurations; different immobilization methods may be employed without departing from the scope of the present invention.

EXAMPLE 1

Affect of CD18 Peptides on Polymorphonuclear Leukocyte Adhesion to Endothelial Cell Monolayers Those peptides shown in Table 1 were synthesized and tested for their capacity to interfere with, or block adhesion of polymorphonuclear leukocytes to human endothelial cell monolayers. These peptides correspond to those underlined in the structure of CD18 shown in FIG. 1. Smaller peptides within a region were also synthesized and tested for activity.

Each peptide is denoted by the number in the figure, that is 1 through 6, and a second number that refers to the number of amino acids in the peptide. Thus, 1–26 refers to a peptide from region 1 with 26 amino acids. Since region 1 consists of only 26 amino acids, 1–26 denotes a peptide that spans the entire region. However, 1–15, refers to a peptide from region 1 consisting of 15 amino acids. The peptides are numbered from the carboxyl to the amino terminal end of the molecule.

Peptides were synthesized using Merrifield's solid-phase method. Merrifield, R. B., 1963, *J. of Amer. Chem. Soc.*, 75:48–79. A Biosearch 9500 automated peptide machine was employed with T-Boc amine protection. Cleavage was performed using hydrogen fluoride, and the resulting peptides were purified by preparative high pressure liquid chromatography using a Walter's Delta-prep 3000 with a PrePak C18 column using an aqueous-acetonitrile-trifluoroacetic acid (TFA) mobile phase.

TABLE 1

| Peptides | CD18 Peptides |
|---|---|
| 1-26: | $NH_2$—Tyr—Pro—Ile—Asp—Leu—Tyr—Tyr—Leu—Met—Asp—Leu—Ser—Tyr—Ser—Met—Leu—Asp—Asp—Leu—Arg—Asn—Val—Lys—Lys—Leu—Gly—COOH |
| 1-15: | $NH_2$—Ser—Tyr—Ser—Met—Leu—Asp—Asp—Leu—Arg—Asn—Val—Lys—Lys—Leu—Gly—COOH |
| 2-24: | $NH_2$—Phe—Asp—Tyr—Pro—Ser—Val—Gly—Gln—Leu—Ala—His—Lys—Leu—Ala—Glu—Asn—Asn—Ile—Gln—Pro—Ile—Phe—Ala—Val—Thr—COOH |
| 2-16: | $NH_2$—Ala—His—Lys—Leu—Ala—Glu—Asn—Asn—Ile—Gln—Pro—Ile—Phe—Ala—Val—Thr—COOH |
| 3-29: | $NH_2$—Ile—Pro—Lys—Ser—Ala—Val—Gly—Glu—Leu—Ser—Glu—Asp—Ser—Ser—Asn—Val—Val—His—Leu—Ile—Lys—Asn—Ala—Tyr—Asn—Lys—Leu—Ser—Ser—COOH |
| 3-17: | $NH_2$—Ser—Ser—Asn—Val—Val—His—Leu—Ile—Lys—Asn—Ala—Tyr—Asn—Lys—Leu—Ser—Ser—COOH |
| 4-29: | $NH_2$—Ile—Gly—Trp—Arg—Asn—Val—Thr—Arg—Leu—Leu—Val—Phe—Ala—Thr—Asp—Asp—Gly—Phe—His—Phe—Ala—Gly—Asp—Gly—Lys—Leu—Gly—Ala—Ile—COOH |
| 4-15: | $NH_2$—Ile—Gly—Trp—Arg—Asn—Val—Thr—Arg—Leu—Leu—Val—Phe—Ala—Thr—Asp—COOH |
| 4-14: | $NH_2$—Asp—Gly—Phe—His—Phe—Ala—Gly—Asp—Gly—Lys—Leu—Gly—Ala—Ile—COOH |
| 5-24: | $NH_2$—Val—Gly—Lys—Gln—Leu—Ile—Ser—Gly—Asn—Leu—Asp—Ala—Pro—Glu—Gly—Gly—Leu—Asp—Ala—Met—Met—Gln—Val—Ala—COOH |
| 5-14: | $NH_2$—Asp—Ala—Pro—Glu—Gly—Gly—Leu—Asp—Ala—Met—Met—Gln—Val—Ala—COOH |
| 6-25: | $NH_2$—Arg—Ile—Gly—Phe—Gly—Ser—Phe—Val—Asp—Lys—Thr—Val—Leu—Pro—Phe—Val—Asn—Thr—His—Pro—Asp—Lys—Leu—Arg—Asn—COOH |
| 6-16: | $NH_2$—Lys—Thr—Val—Leu—Pro—Phe—Val—Asn—Thr—His—Pro—Asp—Lys—Leu—Arg—Asn—COOH |
| WT: | $NH_2$—Cys—Arg—Ile—Ala—Arg—Leu—Glu—Glu—Lys—Val—Lys—Thr—Leu—Lys—Ala—Gln—Asn—Ser—Glu—Leu—Ala—Ser—Thr—Ala—Asn—Met—Leu—Arg—Glu—Gln—Val—Ala—Gln—Leu—Lys—Gln—Lys—Val—Met—Asn—His—Ala—COOH |
| JUN-k: | $NH_2$—Arg—Ile—Ala—Arg—Leu—Lys—Glu—Lys—Val—Lys—Thr—Leu—Lys—Ala—Lys—Asn—Ser—Glu—Leu—Ala—Ser—Thr—Ala—Asn—Met—Leu—Arg—Glu—Gln—Val—Ala—Gln—Leu—Lys—Gln—Lys—Val—Met—Asn—His—Ala—COOH |
| 2X: | $NH_2$—Arg—Ile—Ala—Arg—Leu—Glu—Glu—Lys—Val—Lys—Thr—Leu—Lys—Ala—Glu—Asn—Ser—Glu—Leu—Ala—Ser—Thr—Ala—Asn—Met—Leu—Arg—Glu—Glu—Val—Ala—Gln—Leu—Glu—Gln—Glu—Val—Met—Asn—His—Ala—COOH |

The peptides were lyophilized and stored dessicated at 4° C. until used. At the time a peptide was to be tested for activity, it was weighed out into an Eppendorf tube, and dissolved in about 15–25 μl of dimethyl sulfoxide and then diluted to 250 μl with assay media consisting of RPMI media containing 1% fetal calf serum to give working stock solutions of $4\times10^{-3}$M. If desired, these stock solutions were aliquoted and stored at −70° C. Prior to performing the assay, the $4\times10^{-3}$M stock was diluted in tubes to give final concentrations of $10^{-4}$, $10^{-6}$, $10^{-7}$, and $10^{-8}$M in the assay.

The endothelial cells were isolated from human umbilical cords by mild collagenase digestion. Collagenase was obtained from Worthington Corporation, Freehole, N. J., and the general procedure is described by Jaffe, E. A., et al., 1973, *J. of Clin. Invest.*, 52:2745. The cells obtained from collagenase digestion were grown on gelatin-coated flasks in cell culture medium consisting of medium 199 (Gibco, Grand Island, N.Y.) buffered with 25 mM Hepes. The media was supplemented with 20% fetal calf serum. The media also contained 60 μg/ml sodium heparin (Sigma Corporation, St. Louis, Mo.), 2 mM L-glutamine and 50 μg/ml of bovine hypothalamus extract. The bovine tissue was obtained from Pel Freeze, Rogers, AK. The hypothalamus extract serves as a source of endothelial cell growth factor. The pH of the cell culture media was 7.4.

After the endothelial cells reach confluency, they are passaged with 0.25% trypsin containing 0.02% EDTA, and subsequent subculturing was performed using the same solution. The cells were exposed to this mixture in Hank's balanced salt solution at room temperature for about 1 minute.

Finally, approximately $2\times10^4$ cells/well were seeded in microtiter plates. The endothelial cell nature of the cells was confirmed both by their cobblestone morphology at confluency, and the fact that they stained positive for Factor VIII antigen by indirect immunofluorescence. The latter procedure is well known in the art, and is described by Jaffe, E. A., 1973, *J. Clin. Invest.*, 52:2745.

Monolayers of endothelial cells, prior to the fifth passage, were established on polystyrene, 96-well flat bottom micro titer plates (Corning Corporation) in Medium 199 containing 20% fetal calf serum 25 mM hepes, pH 7.4, and the other supplements described above. The surfaces of the micro titer plates were incubated with 6.4 μg/ml human plasma fibronectin for 30 minutes at 25° C. prior to plating the endothelial cells. The solution of fibronectin was removed before addition of endothelial cells.

The endothelial cell cultures were used when they were confluent. The endothelial monolayers were washed with RPMI plus 1% fetal calf serum and activated with 125 U/ml of TNF, and then incubated with labelled polymorphonuclear leukocytes at a final concentration $5\times10^5$ cells per well. The cells were allowed to settle for 30 minutes onto the endothelial cell monolayers.

Human polymorphonuclear leukocytes were obtained from venus blood from several healthy adult volunteers using an anti-coagulant (10% heparin) followed by centrifugation of the blood on Ficoll-Hypaque gradients. Contaminating erythrocytes were removed by hypotonic lysis. The remaining cell population consisted of 95 to 98% polymorphonuclear leukocytes, and these cells were suspended at a concentration of $50\times10^6$ cells per ml in Hank's balanced salt solution, pH 7.4.

The polymorphonuclear leukocytes were labelled with $^{111}$Indium-oxide (100 μCi/$10^8$ PMNs) (10 mCi/mml, Amersham Corp.). Labelling occurred at room temperature in Hank's solution for 15 minutes, after which the labelled cells were isolated by centrifugation for 5 minutes, and to remove residual unincorporated label, washed twice with Hank's balanced salt solution, and then suspended in RPMI supplemented with 1% fetal calf serum.

As mentioned above, $5\times10^5$ of the labelled PMNs cells were added per well in 96-well micro titer plates. Incubations were conducted for 30 minutes at 37° C., in a tissue culture incubator in an atmosphere of 5% $CO_2$, 95% air.

After the 30 minute incubation period, during which the polymorphonuclear leukocytes adhere to the endothelial cell monolayer, the micro titer plates were filled and sealed with adherent transparent plastic (Dynatech, Inc., Alexander, Va.), inverted and centrifuged using a micro plate carrier, obtainable from Beckman Instruments Corp. Centrifugation was at 75×g for 5 minutes at room temperature. This effectively removed nonadherent PMNs from the endothelial cell monolayers. Next, the plates were blotted dry and the number of polymorphonuclear leukocytes that remained adherent to the endothelial cell monolayers was determined using a gamma counter. The results are shown in Table 2, and they are expressed as the percent of polymorphonuclear leukocytes that remained adherent to the endothelial cell monolayers.

The data shown in Table 2 is instructive in several aspects. Firstly, the most active peptide is 4–29. That is, the number 4 peptide derived from CD 18 that has 29 amino acids. This peptide shows significant inhibitory activity in the PMN adhesion assay. The molecule shows a peak activity in the range of $10^{-5}$ to $10^{-6}$M. Secondly, a 14 amino acid peptide of the number 4 peptide shows little activity. The range of activities for the 29 mer varies over the concentrations tested.

TABLE 2

Summary of Effect of CD18 Peptides on PMN Adhesion to TNF Activated ECs

| Peptides | Average % Change | | | | |
|---|---|---|---|---|---|
| | $10^{-4}$M | $10^{-5}$M | $10^{-6}$M | $10^{-7}$M | $10^{-8}$M |
| 4-29 | −30(10)* | −65(10) | −48(14) | +3(10) | −12(6) |
| 1-26 | −41(6) | −33(3) | −6(7) | +24(3) | +9(6) |
| 1-15 | −24(4) | (ND) | −9(5) | (ND) | −4(4) |
| 2-24 | −79(4) | (ND) | −10(5) | (ND) | −2(4) |
| 2-16 | −7(4) | (ND) | −1(5) | (ND) | −2(4) |
| 3-29 | −58(4) | +12(2) | −5(6) | +27(2) | −2(4) |
| 3-17 | −13(4) | +43(2) | +13(6) | −18(2) | −7(4) |
| 4-14 | −9(4) | +28(4) | −4(8) | +12(4) | −6(4) |
| 5-24 | −17(4) | (ND) | −13(5) | (ND) | −6(4) |
| 5-14 | +9(4) | (ND) | +7(5) | (ND) | 0(4) |
| 6-25 | −13(4) | (ND) | +8(5) | (ND) | +12(4) |
| 6-16 | +6(4) | (ND) | −11(5) | (ND) | −25(4) |
| WT | −54(2) | 0(2) | +22(6) | +8(2) | −15(2) |
| JUN-k | −25(2) | −15(2) | +3(2) | −7(2) | (ND) |
| 2X | −38(2) | −1(2) | −18(4) | −23(2) | −20(2) |

*(# Donors, Variation Between Different PMN Donors was About ±20%)

A significant number of the peptides exhibited activity at $10^{-4}$M, but little or no activity at lower concentrations, and none of the peptides were as active as 4–29 over the range of $10^{-5}$ to $10^{-6}$M. The 26 amino acid peptide of the number 1 peptide of CD18 (1–26) shows inhibitory activity with an apparent peak in the range of $10^{-4}$ to $10^{-5}$M. Similarly, the 24 amino acid peptide of the number 2 region of CD18 (2–24), and 3-29, show activity at $10^{-4}$M. The peptides that showed little inhibitory activity are derived from the fifth and sixth regions of the molecule and contain 14 or 24, or 16 or 25 amino acids, respectively.

Finally, it was observed that the JUN-k, and WT peptides inhibited polymorphonuclear leukocyte adhesion at a concentration range of $10^{-4}$M, while the peptide 2X had activity over a concentration range of $10^{-4}$ to $10^{-8}$M. The proteins that contain these peptides are known in the art or described by Angel, P., et al., 1988, Nature, 332:166.

Studies were conducted using the peptide 4–29 with the intent of determining what effect polymorphonuclear leukocytes from different individuals would have on the effectiveness of the peptide in the adhesion assay. Also the stability of the peptide to various storage conditions was determined. The results are shown in Table III.

Experiments using polymorphonuclear leukocytes isolated from donors 100 and 272 indicate that freezing and thawing the peptide does not significantly effect its activity. Moreover, there is significant variation in the activity of the peptide dependent on the donor from which the polymorphonuclear leukocytes were isolated. Finally, Table III also shows that the activity of peptide is maintained after storage for different times at 4° C.

TABLE 3

Comprehensive Summary of CD18 Peptide #4-29 Data Showing Percent Change in PMN Adhesion to TNF Activated ECs

| Donor | Peptide Concentration (M) | | | | | Peptide |
|---|---|---|---|---|---|---|
| # | $10^{-4}$M | $10^{-5}$M | $10^{-6}$M | $10^{-7}$M | $10^{-8}$M | Condition |
| 269 | −29 | (ND) | −68 | (ND) | −13 | 1 day 4° |
| 314 | −32 | (ND) | −76 | (ND) | −4 | " |
| 178 | −64 | (ND) | −67 | (ND) | +2 | fresh |
| 475 | −19 | (ND) | −76 | (ND) | −20 | " |

TABLE 3-continued

Comprehensive Summary of CD18 Peptide #4-29 Data Showing Percent Change in PMN Adhesion to TNF Activated ECs

| Donor # | $10^{-4}$M | $10^{-5}$M | $10^{-6}$M | $10^{-7}$M | $10^{-8}$M | Peptide Condition |
|---|---|---|---|---|---|---|
| 121 | −14 | −59 | −44 | +3 | −15 | frozen |
| 390 | −16 | −43 | −9 | 0 | −22 | " |
| 593 | (ND) | −86 | −14 | +14 | (ND) | fresh, or 4° for 2 wks |
| 323 | (ND) | −42 | −53 | +45 | (ND) | fresh, or 4° for 2 wks |
| 155* | (ND) | −29 | −13 | +59 | (ND) | 1 wk 4° |
| 272* | (ND) | −71 | −14 | +2 | (ND) | 1 wk 4° |
| 100 | −1 | −63 | −51 | −8 | (ND) | fresh |
| 100 | −38 | −81 | −68 | −29 | (ND) | frozen |
| 272 | −36 | −62 | −59 | −13 | (ND) | fresh |
| 272 | −55 | −80 | −62 | −40 | (ND) | frozen |
| 108 | −16 | −63 | −19 | −2 | −1 | frozen |
| 489 | −31 | −72 | −27 | −15 | −12 | frozen |
| 108* | −68 | −87 | −32 | −2 | +21 | frozen |
| 489* | −37 | −79 | −37 | −7 | −3 | frozen |
| 155 | −7 | −57 | −41 | +1 | (ND) | fresh |
| 272 | +53 | −48 | −41 | +42 | (ND) | fresh |

*endothelial cells were activated with IL-1.

Additional studies were conducted with 4–29 with the intent of determining if a shorter peptide within this region would have activity. Since 4–14 was shown to have little activity, 4–15 was tested and the results are shown in Table 4. Clearly, 4–15 is active, with the peak of activity being in the $10^4$ to $10^{-5}$M range. Variability in the assay was observed as a function of the donor from which the PMNs were isolated.

TABLE 4

Percent Change of Adhesion

| Donor | $10^{-4}$M | $10^{-5}$M | $10^{-6}$M |
|---|---|---|---|
| 155 | −74 | −53 | −23 |
| 272 | −73 | −70 | −19 |
| 279 | −45 | −26 | −12 |
| 279 | −63 | −21 | −20 |
| 499 | −36 | −36 | −9 |
| Average | −58 ± 7 | −41 ± 8 | −17 ± 2 |
| **Donor** | **$10^{-5}$M** | **$10^{-5}$M** | **$10^{-6}$M** |
| 140 | −50 | −6 | −6 |
| 195 | 70 | 0 | 2 |
| 363 | −13 | −18 | −14 |
| 515 | −5 | 4 | −10 |
| 140 | −53 | 0 | 24 |
| Average | −24 ± 10 | −5 ± 3 | −6 ± 2 |

EXAMPLE 2

Effect of CD18 Peptides on Chemotaxis of Polymorphonuclear Leukocytes

Many of the materials and methods used to test the inhibitory activity of the CD18 peptides on the chemotactic response of the polymorphonuclear leukocytes are similar or identical to those used to perform the adhesion assays described in Example 1. Polymorphonuclear leukocytes were isolated and labelled with $^{111}$Indium as described before, and the cells were suspended in RPMI 1640 culture medium at a concentration of $5\times10^6$/ml. Next, 75 μl of the cell suspension and 25 μl of media containing a desired concentration of a CD18 peptide were added to trans-well inserts, and the mixture was incubated at 37° C. for 10 minutes.

To the bottom wells of the 24-well plate 0.6 ml of media containing 0.5% zymosan-activated human serum was added. This solution was also warmed to 37° C. for 10 minutes prior to use.

Next, the assay was conducted by incubating the trans-well inserts containing the cell suspension with the desired CD18 peptide in the 24-well plates at 37° C. for 30 minutes. Subsequently, the inserts were removed, and 60 μl of a 10% sodium dodecyl sulphate solution was added to the wells of the 24-well plate. The plates were incubated with gentle shaking at room temperature for 15 minutes, and 110 μl aliquots were removed and the amount of $^{111}$Indium determined using a gamma-counter.

Table 5 shows the results, which are expressed as the percent inhibition or enhancement of migration caused by the peptides over a concentration range of $10^{-4}$ to $10^6$M. The data were gathered from polymorphonuclear leukocytes isolated from four different human donors numbered 591,593, 195 and 499. It is immediately apparent upon reviewing the data that there is a marked inhibition of chemotaxis migration at concentrations ranging from $10^{-4}$–$10^{-5}$M for peptides 2-24, 3-29 and 4-29. Maximum inhibition is a function both of the concentration of the peptide tested, as well as the donor from which the polymorphonuclear leukocytes were isolated.

TABLE 5

Chemotaxis Summary CD18 Peptides*

| Peptide[M] | | Donors 591 | 593 | 195 | 499 |
|---|---|---|---|---|---|
| 1-26 | $10^{-4}$M | −9 | −50 | 19 | 8 |
| | $10^{-5}$M | −36 | −19 | −41 | −3 |
| | $10^{-6}$M | −39 | −14 | −37 | 13 |
| 2-24 | $10^{-4}$M | −73 | −89 | −48 | −77 |
| | $10^{-5}$M | −9 | −40 | −33 | −33 |
| | $10^{-6}$M | −17 | −22 | 22 | 0 |
| 3-29 | $10^{-4}$M | −57 | −85 | −7 | −33 |
| | $10^{-5}$M | −6 | −17 | 11 | 23 |
| | $10^{-6}$M | 11 | −6 | −26 | −10 |
| 4-29 | $10^{-4}$M | −74 | −88 | −93 | −87 |
| | $10^{-5}$M | −88 | −88 | −93 | −79 |
| | $10^{-6}$M | 0 | 4 | 11 | 0 |
| 5-24 | $10^{-4}$M | 51 | −33 | −52 | 0 |
| | $10^{-5}$M | 55 | 12 | −56 | −15 |
| | $10^{-6}$M | 52 | −4 | −22 | −26 |
| 6-25 | $10^{-4}$M | −16 | −51 | −4 | −3 |
| | $10^{-5}$M | 49 | 26 | 11 | −13 |
| | $10^{-6}$M | 49 | 20 | −44 | −8 |

*Data are expressed as the percent inhibition (−) or enhancement of polymorphonuclear leukocyte migration.

Partly because of the variation in the results observed using polymorphonuclear leukocytes from different individuals, additional experiments were done to confirm the inhibitory effects of the most active peptide, 4–29. The experiments were done using polymorphonuclear leukocytes from 6 donors, with one of the donors, 195, being used here and in the previous experiment. Furthermore, the experiments were conducted over a concentration range of $10^{-4}$–$10^{-7}$. Table 6 shows the results. The inhibitory activity of the peptide was confirmed, with significant activity being observed for all donors. The peak of activity is at $10^{-5}$M. It should be noted, as was observed in the previous experiment, that there is variation in the percent inhibition using polymorphonuclear leukocytes from different donors.

TABLE 6

Effect of CD18 Peptide 4-29 on Neutrophil Chemotaxis

| | Peptide Concentration | | | |
|---|---|---|---|---|
| | $10^{-4}$M | $10^{-5}$M | $10^{-6}$M | $10^{-7}$M |
| Donor | (% Inhibition of Migration)[a] | | | |
| 140 | 83 | 69 | 2 | 0 |
| 279 | 74 | 49 | 17 | 0 |
| 169 | — | 75 | — | — |
| 359 | — | 74 | — | — |
| 195 | 76 | 87 | 34 | — |
| 363 | 76 | 79 | 34 | — |

[a]Measured by total numbers of cell that have migrated through the filter in response to 0.5% zymosan-activated human serum.

EXAMPLE 3

Inhibition of Rhinovirus Binding to Endothelial Cells

The peptide 4–29 can be tested for the capacity of inhibiting rhinovirus binding to activated endothelial cells using the assay described in Example 1, and additionally having present in the assay mixture varying amounts of the peptide and about $1\times10^4$ counts per minute of labelled rhinovirus. Radiolabelled virus may be produced as described by Abraham, G. and Colonno, R. J., 1984, J. Virol., 51:340, with modifications as described by Marlin, S. D. et al., 1990, Nature, 344:70. The endothelial cells are preincubated with 4–29 for 30 minutes at 4° C. to prevent endocytosis of the peptide. It would be determined that a concentration of about 50–100 μg/ml would provide for about 50% inhibition of rhinovirus binding.

EXAMPLE 4

Prophylactic use of CD18 Peptide (4–29) for Preventing Colds

The CD18 peptide 4–29 can be applied for the efficacious prevention of common colds by formulating it in a pharmaceutically acceptable nasal carrier in an effective amount. The amount can be empirically determined by those skilled in the art, but will generally be in the range of about 50 μg-1 mg/ml. Nasal pharmaceutical formulations are well known to those skilled in the art, and are detailed in "Remington's Pharmaceutical Sciences", 14th Edition, 1970. It will be appreciated, however, that the choice of a suitable carrier will depend on the nature of the particular nasal dosage form desired. That is, whether the peptide will be formulated as a nasal solution for use as drops or spray, a nasal suspension, a nasal ointment, or a nasal gel. Preferred is a nasal dosage form consisting of a solution, suspensions and gels, in which peptide 4–29 is present in a physiologically compatible solution. The solution may also contain minor amounts of emulsifiers or dispersing agents, buffering agents, preservatives, wetting agents and gelling agents as are known in the art.

Peptide 4–29 in nasal spray form may be applied by an individual prior to, or immediately after being exposed to other individuals that have a cold. In this way, the exposure of an individual to rhinovirus by an infected individual can be minimized or eliminated since the peptide 4–29 would prevent or greatly reduce the amount of virus that binds to nasal endothelial.

The present invention has been described with reference to specific embodiments. However, this application is intended to cover those changes and substitutions which may be made by those skilled in the art without departing from the spirit and the scope of the appended claims.

We claim:

1. A peptide selected from the group consisting of:

a) $NH_2$—Try—Pro—Ile—Asp—Leu—Tyr—Tyr—Leu—Met—Asp—Leu—Ser—Tyr—Ser—MET—Leu—Asp—Asp—Leu—Arg—Asn—Val—Lys—Lys—Leu—Gly—COOH;

b) $NH_2$—Phe—Asp—Tyr—Pro—Ser—Val—Gly—Gln—Leu—Ala—His—Lys—Leu—Ala—Glu—Asn—Asn—Ile—Gln—Pro—Ile—Phe—Ala—Val—Thr—COOH;

c) $NH_2$—Ile—Pro—Lys—Ser—Ala—Val—Gly—Glu—Leu—Ser—Glu—Asp—Ser—Ser—Asn—Val—Val—His—Leu—Ile—Lys—Asn—Ala—Tyr—Asn—Lys—Leu—Ser—Ser—COOH;

d) $NH_2$—Ile—Gly—Trp—Arg—Asn—Val—Thr—Arg—Leu—Leu—Val—Phe—Ala—Thr—Asp—Asp—Gly—Phe—His—Phe—Ala—Gly—Asp—Gly—Lys—Leu—Gly—Ala—Ile—COOH;

e) $NH_2$—Val—Gly—Lys—Gln—Leu—Ile—Ser—Gly—Asn—Leu—Asp—Ala—Pro—Glu—Gly—Gly—Leu—Asp—Ala—Met—Met—Gln—Val—Ala—COOH; and f) $NH_2$—Arg—Ile—Gly—Phe—Gly—Ser—Phe—Val—Asp—Lys—Thr—Val—Leu—Pro—Phe—Val—Asn—Thr—His—Pro—Asp—Lys—Leu—Arg—Asn—COOH.

2. A peptide as described in claim 1, wherein said peptide is: $NH_2$—Try—Pro—Ile—Asp—Leu—Tyr—Tyr—Leu—Met—Asp—Leu—Ser—Tyr—Ser—Met—Leu—Asp—Asp—Leu—Arg—Asn—Val—Lys—Lys—Leu—Gly—COOH.

3. A peptide as described in claim 1, wherein said peptide is: $NH_2$—Phe—Asp—Tyr—Pro—Ser—Val—Gly—Gln—Leu—Ala—His—Lys—Leu—Ala—Glu—Asn—Asn—Ile—Gln—Pro—Ile—Phe—Ala—Val—Thr—COOH.

4. A peptide as described in claim 1, wherein said peptide is: $NH_2$—Ile—Pro—Lys—Ser—Ala—Val—Gly—Glu—Leu—Ser—Glu—Asp—Ser—Ser—Asn—Val—Val—His—Leu—Ile—Lys—Asn—Ala—Tyr—Asn—Lys—Leu—Ser—Ser—COOH.

5. A peptide as described in claim 1, wherein said peptide is: $NH_2$—Ile—Gly—Trp—Arg—Asn—Val—Thr—Arg—Leu—Leu—Val—Phe—Ala—Thr—Asp—Asp—Gly—Phe—His—Phe—Ala—Gly—Asp—Gly—Lys—Leu—Gly—Ala—Ile—COOH.

6. A peptide as described in claim 1, wherein said peptide is: $NH_2$—Val—Gly—Lys—Gln—Leu—Ile—Ser—Gly—Asn—Leu—Asp—Ala—Pro—Glu—Gly—Gly—Leu—Asp—Ala—Met—Met—Gln—Val—Ala—COOH.

7. A peptide as described in claim 1, wherein said peptide is: $NH_2$—Arg—Ile—Gly—Phe—Gly—Ser—Phe—Val—Asp—Lys—Thr—Val—Leu—Pro—Phe—Val—Asn—Thr—His—Pro—Asp—Lys—Leu—Arg—Asn—COOH.

8. A method for treating inflammation said method comprising the step of administering to a subject in need thereof, an effective amount of a peptide selected from the group consisting of:

a) $NH_2$—Tyr—Pro—Ile—Asp—Leu—Tyr—Tyr—Leu—Met—Asp—Leu—Ser—Tyr—Ser—Met—Leu—Asp—Asp—Leu—Arg—Asn—Val—Lys—Lys—Leu—Gly—COOH;

b) $NH_2$—Phe—Asp—Tyr—Pro—Ser—Val—Gly—Gln—Leu—Ala—His—Lys—Leu—Ala—Glu—Asn—Asn—Ile—Gln—Pro—Ile—Phe—Ala—Val—Thr—COOH;

c) $NH_2$—Ile—Pro—Lys—Ser—Ala—Val—Gly—Glu—Leu—Ser—Glu—Asp—Ser—Ser—Asn—Val—Val—His—Leu—Ile—Lys—Asn—Ala—Tyr—Asn—Lys—Leu—Ser—Ser—COOH;

d) $NH_2$—Ile—Gly—Trp—Arg—Asn—Val—Thr—Arg—Leu—Leu—Val—Phe—Ala—Thr—Asp—Asp—Gly—Phe—His—Phe—Ala—Gly—Asp—Gly—Lys—Leu—Gly—Ala—Ile—COOH;

e) $NH_2$—Val—Gly—Lys—Gln—Leu—Ile—Ser—Gly—Asn—Leu—Asp—Ala—Pro—Glu—Gly—Gly—Leu—Asp—Ala—Met—Met—Gln—Val—Ala—COOH; and f) $NH_2$—Arg—Ile—Gly—Phe—Gly—Ser—Phe—Val—Asp—Lys—Thr—Val—Leu—Pro—Phe—Val—Asn—Thr—His—Pro—Asp—Lys—Leu—Arg—Asn—COOH.

9. A peptide selected from the group consisting of $NH_2$—Cys—Arg—Ile—Ala—Arg—Leu—Glu—Glu—Lys—Val—Lys—Thr—Leu—Lys—Ala—Gln—Asn—Ser—Glu—Leu—Ala—Ser—Thr—Ala—Asn—Met—Leu—Arg—Glu—Gln—Val—Ala—Gln—Leu—Lys—Gln—Lys—Val—Met—Asn—His—Ala—COOH, $NH_2$—Arg—Ile—Ala—Arg—Leu—Lys—Glu—Lys—Val—Lys—Thr—Leu—Lys—Ala—Lys—Asn—Ser—Glu—Leu—Ala—Ser—Thr—Ala—Asn—Met—Leu—Arg—Glu—Gln—Val—Ala—Gln—Leu—Lys—Gln—Lys—Val—Met—Asn—His—Ala—COOH, $NH_2$—Arg—Ile—Ala—Arg—Leu—Glu—Glu—Lys—Val—Lys—Thr—Leu—Lys—Ala—Glu—Asn—Ser—Glu—Leu—Ala—Ser—Thr—Ala—Asn—Met—Leu—Arg—Glu—Glu—Val—Ala—Gln—Leu—Glu—Gln—Glu—Val—Met—Asn—His—Ala—COOH.

* * * * *